United States Patent [19]

Cullinan et al.

[11] Patent Number: 5,391,557
[45] Date of Patent: Feb. 21, 1995

[54] METHODS FOR THE TREATMENT OF PERI-MENOPAUSAL SYNDROME

[75] Inventors: George J. Cullinan, Trafalgar; John D. Termine, Indianapolis, both of Ind.

[73] Assignee: Eli Lilly and Company, Indianapolis, Ind.

[21] Appl. No.: 138,287

[22] Filed: Oct. 15, 1993

[51] Int. Cl.$^6$ .................. A61K 31/445; A61K 31/40; A61K 31/38
[52] U.S. Cl. .................................... 514/324; 514/422; 514/443
[58] Field of Search ..................... 514/324, 422, 443

[56] References Cited

U.S. PATENT DOCUMENTS

| | | | |
|---|---|---|---|
| 4,133,814 | 1/1979 | Jones et al. | 544/146 |
| 4,380,635 | 4/1983 | Peters | 546/202 |
| 4,418,068 | 11/1983 | Jones | 546/237 |
| 5,075,321 | 12/1991 | Schreiber | 514/317 |

FOREIGN PATENT DOCUMENTS

WO93/10113 5/1993 Japan.
WO93/1074 6/1993 WIPO.

OTHER PUBLICATIONS

Draper et al., "Effects of Raloxifene (LY139481 HCl) on Biochemical Markers of Bone and Lipid Metabolism i Healthy Postmenopausal Women", Hong Kong, Fourth Int'l Symp. on Osteoporosis, Mar. 29, 1993.
Bryant et al., "Protection from Bone Loss and Lowering of Serum Cholesterol in the Absence of Uterine Stimulation in Ovariectomized Rats", Am Soc. Bone & Min. Res., Tampa, Sep. 18–22, 1993.
Bryant et al., "Raloxifene is a Tissue Specific Estrogen Agonist", Am Soc. Bone & Min. Res., Tampa, Sep. 18–22, 1993.
Frolick et al., "In Vivo and In Vitro Metabolism of Raloxifene", Am. Soc. Bone & Min. Res., Tampa, Sep. 18–22, 1993.
Glasebrook et al., "Multiple Binding Sites for the Anti–estrogen Raloxifene", Am Soc. Bone & Min. Res., Tampa, Sep. 18–22, 1993.
Hock et al., "Combination of Raloxifene and Human Parathyoid Hormone 1-34; Increased Femur Bone Mass in Young Ovariectomized (OVX) Rats", Am. Soc. Bone & Min. Res., Tampa, Sep. 18–22, 1993.
Sato et al., "DEXA Analysis of Raloxifene Effects on the Bones From Ovariectomized Rats", Am. Soc. for Bone and Min. Res., Tampa, Sep. 18–22, 1993.

(List continued on next page.)

Primary Examiner—Raymond J. Henley, III
Assistant Examiner—Kimberly R. Jordan
Attorney, Agent, or Firm—James J. Sales; Gerald V. Dahling

[57] ABSTRACT

A method of treating peri-menopasual syndrome comprising administering to a human in need of treatment an effective amount of a compound having the formula

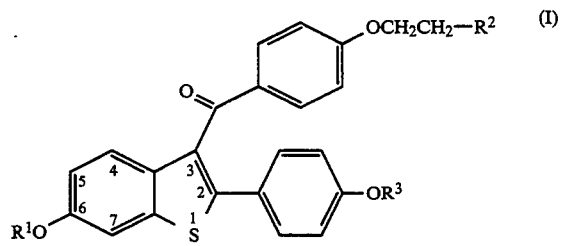

wherein $R^1$ and $R^3$ are independently hydrogen, —$CH_3$,

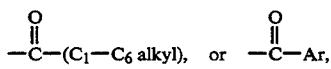

wherein Ar is optionally substituted phenyl;
$R^2$ is selected from the group consisting of pyrrolidine and piperidino; or a pharmaceutically acceptable salt of solvate thereof.

3 Claims, No Drawings

OTHER PUBLICATIONS

Yang et al., "Raloxifene and Anti-Estrogen, Simulates the Effects of Estrogen in Inhibiting Bone Resorption Through Regulating TGFB-3 Expression in Bone;" Am. Soc. for Bone and Min. Res., Tampa, Sep. 18-22, 1993.

Black et al., "Distinct, Structure-Related Profiles of Estrogenic and Anti-Estrogenic Activity in the Tamoxifen and LY117018 Series;" The Endocrine Society, Abstract 1982.

Black et al., "Uterine Bioassay of Tamoxifen, Trioxifene, and New Estrogen Antagonist (LY117018) in Rats and Mice," Life Sciences, 26:1980, 1453-1458.

Black et al., "Differential Interaction of Antiestrogens with Cytosol Estrogen Receptors," Molecular and Cellular Endocrinology, 22:1981, 95-103.

Black et al., "Evidence for Biological Action of the Antiestrogens LY117018 and Tamoxifen by Different Mechanisms," Endocrinology 109;1982, 987-989.

Black, L. J. "Biological Actions and Binding Properites of a New Estrogen Antagosist LY117018," In: Homone Antagonists, 129-82, 1982 (M. K. Agarwal ed.) Walter de Gruyter and Co., Berlin New York.

Black et al., LY156758: A Unique Antiestrogen Displaying High Affinity for Estrogen Receptors, Negligible Estrogenic Activity and Near-Total Estrogen Antagonism in Vivo. Presented at the Fifth Annual San Antonio Breast Cancer Symposium, San Antonio, Texas, Nov. 5-6, 1982.

Black et al., The Antiestrogenic Action of LY139481: Species Uniformity Duration of Action and Kinetics of 3H-LY139481 Distribution In Vivo. Sixty-fifth Annual Meeting of the Endocrine Society, San Antonio, Texas, Jun. 8-10, 1983, abs. 93.

Black et al., Antagonism of Estrogen Action with a New benzothiophene Derived Antiestrogen, Life Sciences 32:1983. 1031-1036.

Black et al., The Relationship of the Antiestrogenic Efficacy of LY156758 to its Pharmacokinetics and Metabolism Following Oral Administration to Adult Ovariectomized Rats, Seventh International Congress of Endocrinology, Quebec City, Canada, Jul. 1-7, 1984, abs. 323.

Black et al., Synthesis and Antiestrogenic Activity of [3,4-Dihydro-2(4-methoxyphenyl)-1-napthalenyl] [4-[2-pyrrolidinyl) ethoxyl]-phenyl] methanone, methanesulfonic acid salt, Journal of Medicinal Chemistry 22; 1979, 962-966.

Black et al., Antiestrogens 2. Structure Activity Studies in a Series of 3-Aroyl-2-arylbenzo[b]thiophene Derivatives Leading to [6-Hydroxy-2-(4-hydroxyphenyl)-benzo[b]thien-3-yl][4-[2-(1-piperidinyl(ethoxy]--phenyl]methanone Hydrochloride (LY156758), a Remarkably Effective Estrogen Antagonist with Only Minimal Intrinsic Estrogenicity, J. Med. Chem. 27(8), 1984, 1057-1066.

U.S. Ser. No. 07/920,933 to Black et al., Jul. 28, 1992.
U.S. Ser. No. 07/995,222 to Black et al., Dec. 22, 1992.
U.S. Ser. No. 08/035,121 to Black et al. Mar., 19, 1993.
U.S. Ser. No. 08/2218 to Cullinan et al. Jun. 24, 1993.
U.S. Ser. No. 08/096,480 to Hock, Jul. 22, 1993.
U.S. Ser. No. 08/112,012 to Dodge et al., Aug. 15, 1993.
U.S. Ser. No. 08/111,796 to Dodge et al., Aug. 25, 1993.

METHODS FOR THE TREATMENT OF PERI-MENOPAUSAL SYNDROME

BACKGROUND OF THE INVENTION

The terms peri-menopausal refers to that time in a women's life between pre-menopause (the reproductive years) and post-menopause. This time period is usually between the ages of 40–60, but more often several years on either side of 50 years of age. This period is characterized by a rapid change in the hormonal balance in a woman. Although many different hormones are subject to rapid fluctuation during this time, the most notable are sex related hormones and in particular estrogens and to a lesser extent progestins. The cause of this fluctuation is the natural and time dependent cessation of ovian function. The hallmark of the ending of the peri-menopausal period and the beginning of the post-menopausal period is the cessation of ovian function or its inability to regulate the previously normal ovulation cycle in the woman. This cessation of function is clinically marked by the cessation of mensus of a period of one year or more. The time period over which this cessation of ovian function persists, i.e., the peri-menopausal time, is usually not a sudden or rapid event. The peri-menopausal state can last from a few months to more typically a year or more.

As mentioned before the peri-menopause is marked by fluctuations in the woman's hormonal composition, and these fluctuations are marked with many sequellae. Sometimes these sequellae pass without undo problems for the woman; however, they are often a source of moderate to severe discomfort and concern and are occasionally the source of pathological or even life-threatening events.

It is these sequellae in the peri-menopause time which define the syndrome. A list of common, through highly idiosyncratic, sequellae resulting from entering the peri-menopause are: Hot flashes and sweats, atrophic vaginitis, headache, dizziness, lack of concentration, irritability, loss of libido, joint pain, sleeplessness, apathy, lassitude, muscular weakness,-and palpitations. ("The Menopause", Ed. R. J. Beard, University of Park Press, 1976, Chapter 11). In addition, there has been described a "menopausal or peri-menopausal syndrome" marked with depression. Although there is some controversy as to whether this is a true psychiatric syndrome or not, the peri-menopause is a contributing factor. ("Harrison's principles of Internal Medicine", Ed. N. J. Isselbacher, et al., 9th ed., McGraw-Hill Book Co., 1980 pp. 1782–1783). In extreme cases, some of these sequellae in some women are pathological (such as fluid retention and imbalance) and even life-threatening, especially in those women predisposed to the effects of depression. However, for most women, a major cause of discomfort and concern lies not so much in the occurrence of one of more of these events, but the length of time which they must bear them and their unpredictable nature.

Since it would be unreasonable to believe that any treatment can turn back the course of aging, the clinical approach to the treatment of peri-menopausal syndrome has been one of amelioration. Specifically, the peri-menopausal woman in need of treatment is given a deescalating protocol of exogenous estrogen. This has the effect of bringing the patient slowly to the state of post-menopause, because although the exogenous estrogen effectively treats the symptoms of peri-menopause, it does not stop the inexorable decline in ovian function. Often, this de-escalation therapy requires a protracted period of time (as much as several years, in extreme cases) in order to allow the ovian function to cease by the time the exogenous estrogen is terminated. Although this therapy is effective and approved, it does carry many side-effects.

The side-effects usually associated with estrogen therapy are due not only to the estrogen, but also with the con-combinant progestins. In most cases, women with a uterus must be given estrogen and a progestin either together or more commonly in a cyclic protocol. The reason for this co-administration is to reduce the risk of endometrial cancer which estrogen given alone posses. The effects of the progestin are often poorly tolerated by many women, causing depression or even negating the salutory effects of the estrogen. The estrogen, itself, often causes unpleasant side-effects such as water retention, weight gain, hypertension, etc. The result is often non-compliance of the patient with the therapy and the subsequent suffering of the peri-menopausal symptoms.

Ideally, an improved therapy would be an agent which would ameliorate the symptoms of peri-menopausal syndrome, but would avoid or lessen the side-effects. Additionally, this ideal therapy would also reduce the period of time to bring the woman into a stable, post-menopausal state.

SUMMARY OF THE INVENTION

This invention provides methods for treating peri-menopausal syndrome, comprising administering to a human in need of treatment an effective amount of a compound of formula I

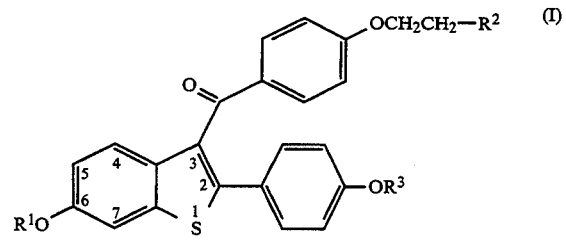

wherein $R^1$ and $R^3$ are independently hydrogen, —CH$_3$,

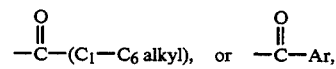

wherein Ar is optionally substituted phenyl;
$R^2$ is selected from the group consisting of pyrrolidino and piperidino; and pharmaceutically acceptable salts and solvates thereof.

DETAILED DESCRIPTION OF THE INVENTION

The current invention concerns the discovery that a select group of 2-phenyl-3-aroylbenzothiophenes (benzothiophenes), those of formula I, are useful for treating peri-menopausal syndrome. The methods of treatment provided by this invention are practiced by administering to a human in need, a dose of a compound of formula I or a pharmaceutically acceptable salt or solvate thereof, that is effective to treat peri-menopausal syndrome. Treating is defined to include ameliorating one or more of the symptoms of peri-menopausal syndrome, and/or bringing a woman into a stable post-menopausal state in a reduced period of time.

Generally, the compound is formulated with common excipients, diluents or carriers, and compressed into tablets, or formulated as elixirs or solutions for convenient oral administration, or administered by the intramuscular or intravenous routes. The compounds can be administered transdermally, and may be formulated as sustained release dosage forms and the like.

The compounds used in the methods of the current invention can be made according to established procedures, such as those detailed in U.S. Pat. Nos. 4,133,814, 4,418,068, and 4,380,635 all of which are incorporated by reference herein. In general, the process starts with a benzo[b]thiophene having a 6-hydroxyl group and a 2(4-hydroxyphenyl) group. The starting compound is protected, alkylated, and deprotected to form the formula I compounds. Examples of the preparation of such compounds are provided in the U.S. patents discussed above. Substituted phenyl includes phenyl substituted once or twice with $C_1$–$C_6$ alkyl, $C_1$–$C_4$ alkoxy, hydroxy, nitro, chloro, fluoro, or tri(chloro or fluoro) methyl.

The compounds used in the methods of this invention form pharmaceutically acceptable acid and base addition salts with a wide variety of organic and inorganic acids and bases and include the physiologically acceptable salts which are often used in pharmaceutical chemistry. Such salts are also part of this invention. Typical inorganic acids used to form such salts include hydrochloric, hydrobromic, hydroiodic, nitric, sulfuric, phosphoric, hypophosphoric and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, $\beta$-hydroxybutyrate, butyne-1,4-dioate, hexyne-1,4-dioate, caprate, caprylate, chloride, cinnamate, citrate formate, fumarate, glycollate, heptanoate, hippurate, lactate, malate, maleate, hydroxymaleate, malonate, mandelate, mesylate, nicotinate, isonicotinate, nitrate, oxalate, phthalate, teraphthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzene-sulfonate, p-bromophenylsulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like. A preferred salt is the hydrochloride salt.

The pharmaceutically acceptable acid addition salts are typically formed by reacting a compound of formula I with an equimolar or excess amount of acid. The reactants are generally combined in a mutual solvent such as diethyl ether or benzene. The salt normally precipitates out of solution within about one hour to 10 days and can be isolated by filtration or the solvent can be stripped off by conventional means.

Bases commonly used for formation of salts include ammonium hydroxide and alkali and alkaline earth metal hydroxides, carbonates and bicarbonates, as well as aliphatic and primary, secondary and tertiary amines, aliphatic diamines and hydroxy alkylamines. Bases especially useful in the preparation of addition salts include ammonium hydroxide, potassium carbonate, sodium bicarbonate, calcium hydroxide, methylamine, diethylamine, ethylene diamine, cyclohexylamine and ethanolamine.

The pharmaceutically acceptable salts generally have enhanced solubility characteristics compared to the compound from which they are derived, and thus are often more amenable to formulation as liquids or emulsions.

Pharmaceutical formulations can be prepared by procedures known in the art. For example, the compounds can be formulated with common excipients, diluents, or carriers, and formed into tablets, capsules, suspensions, powders, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinyl pyrrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

The compounds can also be formulated as elixirs or solutions for convenient oral administration or as solutions appropriate for parenteral administration, for instance by intramuscular, subcutaneous or intravenous routes. Additionally, the compounds are well suited to formulation as sustained release dosage forms and the like. The formulations can be so constituted that they release the active ingredient only or preferably in a particular part of the intestinal tract, possibly over a period of time. The coatings, envelopes, and protective matrices may be made, for example, from polymeric substances or waxes.

The particular dosage of a compound of formula I required to treat peri-menopausal syndrome, according to this invention will depend upon the severity of the condition, the route of administration, and related factors that will be decided by the attending physician. Generally, accepted and effective daily doses will be from about 0.1 to about 1000 mg/day, and more typically from about 50 to about 600 mg/day. Such dosages will be administered to a subject in need of treatment from once to about three times each day, or more often as needed to effectively treat peri-menopausal syndrome.

It is usually preferred to administer a compound of formula I in the form of an acid addition salt, as is customary in the administration of pharmaceuticals bearing a basic group, such as the piperidino ring. It is also advantageous to administer such a compound by the oral route to an aging woman. For such purposes the following oral dosage forms are available.

Formulations

In the formulations which follow, "Active ingredient" means a compound of formula I.

| Formulation 1: Gelatin Capsules | |
|---|---|
| Hard gelatin capsules are prepared using the following: | |
| Ingredient | Quantity (mg/capsule) |
| Active ingredient | 0.1–1000 |
| Starch, NF | 0–650 |
| Starch flowable powder | 0–650 |
| Silicone fluid 350 centistokes | 0–15 |

The ingredients are blended, passed through a No. 45 mesh U.S. sieve, and filled into hard gelatin capsules.

Examples of specific capsule formulations of the compound of formula 1 wherein $R^2$ is piperidino, and $R^1$ and $R^3$ are hydrogen, (raloxifene), that have been made include those shown below:

| Formulation 2: Raloxifene capsule | |
|---|---|
| Ingredient | Quantity (mg/capsule) |
| Raloxifene | 1 |
| Starch, NF | 112 |
| Starch flowable powder | 225.3 |
| Silicone fluid 350 centistokes | 1.7 |

| Formulation 3: Raloxifene capsule | |
|---|---|
| Ingredient | Quantity (mg/capsule) |
| Raloxifene | 5 |
| Starch, NF | 108 |
| Starch flowable powder | 225.3 |
| Silicone fluid 350 centistokes | 1.7 |

| Formulation 4: Raloxifene capsule | |
|---|---|
| Ingredient | Quantity (mg/capsule) |
| Raloxifene | 10 |
| Starch, NF | 103 |
| Starch flowable powder | 225.3 |
| Silicone fluid 350 centistokes | 1.7 |

| Formulation 5: Raloxifene capsule | |
|---|---|
| Ingredient | Quantity (mg/capsule) |
| Raloxifene | 50 |
| Starch, NF | 150 |
| Starch flowable powder | 397 |
| Silicone fluid 350 centistokes | 3.0 |

The specific formulations above may be changed in compliance with the reasonable variations provided.

A tablet formulation is prepared using the ingredients below:

| Formulation 6: Tablets | |
|---|---|
| Ingredient | Quantity (mg/tablet) |
| Active ingredient | 0.1–1000 |
| Cellulose, microcrystalline | 0–650 |
| Silicon dioxide, fumed | 0–650 |
| Stearate acid | 0–15 |

The components are blended and compressed to form tablets.

Alternatively, tablets each containing 0.1–1000 mg of active ingredient are made up as follows:

| Formulation 7: Tablets | |
|---|---|
| Ingredient | Quantity (mg/tablet) |
| Active ingredient | 0.1–1000 |
| Starch | 45 |
| Cellulose, microcrystalline | 35 |
| Polyvinylpyrrolidone | 4 |
| (as 10% solution in water) | |
| Sodium carboxymethyl cellulose | 4.5 |
| Magnesium stearate | 0.5 |
| Talc | 1 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 0.1–1000 mg of medicament per 5 mL dose are made as follows:

| Formulation 8: Suspensions | |
|---|---|
| Ingredient | Quantity (mg/5 ml) |
| Active ingredient | 0.1–1000 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified water to | 5 mL |

The medicament is passed through a No. 45 mesh U.S. sieve and mixed with the sodium carboxymethyl cellulose and syrup to form a smooth paste. The benzoic acid solution, flavor, and color are diluted with some of the water and added, with stirring. Sufficient water is then added to produce the required volume.

TEST PROCEDURE

Test 1

A group of 3–20 women between the age of 45–50 years of age are selected as a test group. The women exhibit at least one of the sequellae of impending menopause. A compound of the invention is given in the amount of 100–500 mg/day and the sequellae are closely monitored. The dosing of the compound of %he invention continues for a period of three (3) weeks.

Test 2

The same test as in Test 1 is carried out, however, the administration period is for a time of three (3) months.

Test 3

This test is ran as Test 1, except the dosing period is for a period of six (6) months.

Activity, defined as either total cessation of one or more sequellae of the patient, or reduced severity or occurrence thereof, or a more rapid advancement to menopausal state, in any of the above assays indicates that the compounds of the invention are useful in the treatment of peri-menopausal syndrome.

We claim:

1. A method of treating peri-menopausal syndrome comprising administering to a human in need of treatment an effective amount of a compound having the formula

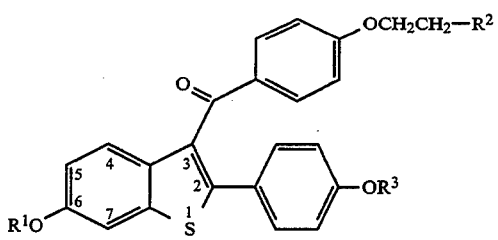

wherein $R^1$ and $R^3$ are independently hydrogen, —CH$_3$,

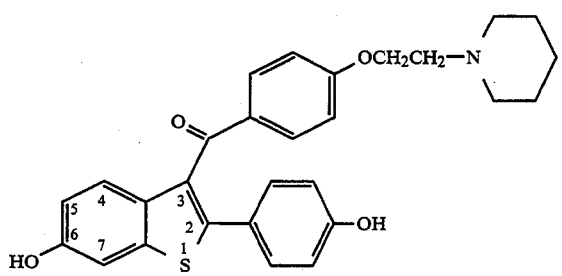

wherein Ar is optionally substituted phenyl;
$R^2$ is selected from the group consisting of pyrrolidine and piperidino; or a pharmaceutically acceptable salt of solvate thereof.

2. The method of claim 1 wherein said compound is the hydrochloride salt thereof.

3. The method of claim 1 wherein said compound or its hydrochloride salt.

* * * * *